US008827978B2

(12) United States Patent
Ellstrom

(10) Patent No.: US 8,827,978 B2
(45) Date of Patent: Sep. 9, 2014

(54) BAG CONNECTOR

(75) Inventor: Anna Ellstrom, Göteborg (SE)

(73) Assignee: Carmel Pharma AB, Gothenburg (SE)

( * ) Notice: Subject to any disclaimer, the term of this patent is extended or adjusted under 35 U.S.C. 154(b) by 651 days.

(21) Appl. No.: 12/678,625

(22) PCT Filed: Sep. 17, 2007

(86) PCT No.: PCT/SE2007/050657
§ 371 (c)(1), (2), (4) Date: Jun. 4, 2010

(87) PCT Pub. No.: WO2009/038505
PCT Pub. Date: Mar. 26, 2009

(65) Prior Publication Data
US 2010/0249745 A1 Sep. 30, 2010

(51) Int. Cl.
*A61B 19/00* (2006.01)
*A61J 1/20* (2006.01)
*A61J 1/10* (2006.01)
*A61J 1/14* (2006.01)

(52) U.S. Cl.
CPC ............ *A61J 1/20* (2013.01); *A61J 2001/2065* (2013.01); *A61J 1/10* (2013.01); *A61J 2001/1481* (2013.01); *A61J 1/1475* (2013.01); *A61J 2001/2051* (2013.01); *A61J 2001/201* (2013.01)
USPC ........................................... 604/415; 206/438

(58) Field of Classification Search
CPC ............ A61M 5/162; A61J 1/10; A61J 1/12; A61J 1/14; A61J 1/20; A61J 1/121; A61J 1/1406; A61J 1/2089; A61J 1/2096; B65D 51/00; B65D 51/002
USPC .................. 604/403, 411, 414, 415, 533–535
See application file for complete search history.

(56) References Cited

U.S. PATENT DOCUMENTS 1,844,342 A 2/1932 Berman
2,010,417 A 8/1935 Schwab (Continued)

FOREIGN PATENT DOCUMENTS

AU 200112863 5/2003
DE 2005519 10/1979

(Continued)

OTHER PUBLICATIONS

Taiwan Search Report for Taiwan Patent Application 092106323 dated Mar. 21, 2003 (4 pages).

(Continued)

*Primary Examiner* — Melanie Hand
(74) *Attorney, Agent, or Firm* — Serville Whitney LLC

(57) ABSTRACT

The present invention concerns an attachable membrane device for providing a piercable liquid barrier membrane to the surface of a pierceable fluid container, such as an infusion bag. The attachable membrane device have a fastening part comprising a fastening surface adapted to be attached to the surface of the pierceable fluid container and thereby provide a liquid tight seal between the fastening surface and the surface of the pierceable fluid container. Additionally, the attachable membrane device is further provided with a barrier membrane part, adapted to provide a liquid tight seal after penetration by a piercing member. Connection means is arranged to the attachable membrane device. The invention simplifies the injection or withdrawal of a fluid in a pierceable fluid container.

19 Claims, 3 Drawing Sheets

(56) References Cited

U.S. PATENT DOCUMENTS

| | | | |
|---|---|---|---|
| 2,697,438 | A | 12/1954 | Hickey |
| 2,717,599 | A | 9/1955 | Huber |
| 3,064,651 | A | 11/1962 | Henderson |
| 3,071,135 | A | 1/1963 | Baldwin et al. |
| 3,306,563 | A | 2/1967 | Soto, Ricardo Hurtado |
| 3,308,822 | A | 3/1967 | DeLuca |
| 3,316,908 | A | 5/1967 | Burke |
| 3,340,671 | A | 9/1967 | Loo |
| 3,390,677 | A | 7/1968 | Razimbaud |
| 3,448,740 | A | 6/1969 | Figge |
| 3,542,240 | A | 11/1970 | Solowey |
| 3,783,895 | A | 1/1974 | Weichselbaum |
| 3,788,320 | A | 1/1974 | Dye |
| 3,822,700 | A | 7/1974 | Pennington |
| 3,938,520 | A | 2/1976 | Scislowicz et al. |
| 3,976,073 | A | 8/1976 | Quick et al. |
| 4,096,860 | A | 6/1978 | McLaughlin |
| 4,296,786 | A | 10/1981 | Brignola |
| D270,568 | S | 9/1983 | Armstrong |
| 4,490,139 | A | 12/1984 | Huizenga et al. |
| 4,516,967 | A | 5/1985 | Kopfer |
| 4,564,054 | A | 1/1986 | Gustavsson |
| 4,573,967 | A | 3/1986 | Hargrove et al. |
| 4,576,211 | A | 3/1986 | Valentini et al. |
| 4,581,016 | A | 4/1986 | Gettig |
| 4,582,223 | A | 4/1986 | Kobe |
| 4,588,403 | A | 5/1986 | Weiss et al. |
| 4,600,040 | A | 7/1986 | Naslund |
| 4,623,343 | A | 11/1986 | Thompson |
| 4,629,455 | A | 12/1986 | Kanno |
| 4,632,673 | A | 12/1986 | Tiitola et al. |
| 4,636,204 | A | 1/1987 | Christopherson et al. |
| 4,673,400 | A | 6/1987 | Martin |
| 4,673,404 | A | 6/1987 | Gustavsson |
| 4,737,150 | A | 4/1988 | Baeumle et al. |
| 4,752,287 | A | 6/1988 | Kurtz et al. |
| 4,759,756 | A | 7/1988 | Forman et al. |
| 4,768,568 | A | 9/1988 | Fournier et al. |
| 4,792,329 | A | 12/1988 | Schreuder |
| 4,804,015 | A | 2/1989 | Albinsson |
| 4,822,340 | A | 4/1989 | Kamstra |
| 4,826,492 | A | 5/1989 | Magasi |
| 4,834,717 | A | 5/1989 | Haber et al. |
| 4,842,585 | A | 6/1989 | Witt |
| 4,850,978 | A | 7/1989 | Dudar et al. |
| 4,864,717 | A | 9/1989 | Baus, Jr. |
| 4,872,494 | A | 10/1989 | Coccia |
| 4,878,897 | A | 11/1989 | Katzin |
| 4,889,529 | A | 12/1989 | Haindl |
| 4,898,209 | A | 2/1990 | Zbed |
| 4,909,290 | A | 3/1990 | Coccia |
| 4,932,937 | A | 6/1990 | Gustavsson et al. |
| 4,944,736 | A | 7/1990 | Holtz |
| 4,964,855 | A | 10/1990 | Todd et al. |
| 4,982,769 | A | 1/1991 | Fournier et al. |
| 4,994,048 | A | 2/1991 | Metzger |
| 4,997,083 | A | 3/1991 | Loretti et al. |
| 5,017,186 | A | 5/1991 | Arnold |
| 5,875,931 | A | 3/1999 | Py |
| D427,308 | S | 6/2000 | Zinger |
| D445,501 | S | 7/2001 | Niedospial, Jr. |
| 6,761,286 | B2 | 7/2004 | Py et al. |
| D495,416 | S | 8/2004 | Dimeo et al. |
| D506,256 | S | 6/2005 | Miyoshi et al. |
| 7,000,806 | B2 | 2/2006 | Py et al. |
| D570,477 | S | 6/2008 | Gallogly et al. |
| D572,820 | S | 7/2008 | Gallogly et al. |
| D577,438 | S | 9/2008 | Gallogly et al. |
| D577,822 | S | 9/2008 | Gallogly et al. |
| D582,033 | S | 12/2008 | Baxter et al. |
| D605,755 | S | 12/2009 | Baxter et al. |
| D616,984 | S | 6/2010 | Gilboa |
| 2001/0021825 | A1 | 9/2001 | Becker et al. |
| 2001/0025671 | A1 | 10/2001 | Safabash |
| 2002/0002352 | A1 | 1/2002 | Becker et al. |
| 2002/0082586 | A1 | 6/2002 | Finley et al. |
| 2002/0127150 | A1 | 9/2002 | Sasso |
| 2002/0177819 | A1 | 11/2002 | Barker et al. |
| 2003/0010717 | A1 | 1/2003 | Brugger et al. |
| 2003/0070726 | A1 | 4/2003 | Andreasson et al. |
| 2003/0106610 | A1 | 6/2003 | Roos et al. |
| 2003/0107628 | A1 | 6/2003 | Fowles et al. |
| 2003/0199846 | A1 | 10/2003 | Fowles et al. |
| 2003/0233083 | A1* | 12/2003 | Houwaert et al. ............ 604/403 |
| 2004/0116858 | A1 | 6/2004 | Heinz et al. |
| 2004/0199139 | A1 | 10/2004 | Fowles et al. |
| 2004/0215147 | A1 | 10/2004 | Wessman et al. |
| 2005/0184140 | A1* | 8/2005 | DeLa Vergne ................ 229/301 |
| 2005/0215977 | A1 | 9/2005 | Uschold |
| 2006/0025747 | A1 | 2/2006 | Sullivan et al. |
| 2006/0106360 | A1 | 5/2006 | Wong |
| 2006/0111667 | A1 | 5/2006 | Matsuura et al. |
| 2006/0157984 | A1 | 7/2006 | Rome et al. |
| 2006/0186045 | A1 | 8/2006 | Jensen et al. |
| 2007/0021725 | A1 | 1/2007 | Villette |
| 2007/0060841 | A1 | 3/2007 | Henshaw |
| 2007/0088313 | A1 | 4/2007 | Zinger et al. |
| 2007/0106244 | A1 | 5/2007 | Mosler et al. |
| 2007/0179441 | A1 | 8/2007 | Chevallier |
| 2007/0270759 | A1 | 11/2007 | Pessin |
| 2007/0270778 | A9 | 11/2007 | Zinger et al. |
| 2008/0045919 | A1 | 2/2008 | Jakob et al. |
| 2008/0103453 | A1 | 5/2008 | Liversidge |
| 2008/0103485 | A1 | 5/2008 | Kruger |
| 2008/0172039 | A1 | 7/2008 | Raines |
| 2008/0223484 | A1 | 9/2008 | Horppu |
| 2008/0287920 | A1 | 11/2008 | Fangrow et al. |
| 2008/0312634 | A1 | 12/2008 | Helmerson et al. |
| 2009/0254042 | A1 | 10/2009 | Gratwohl et al. |
| 2010/0137827 | A1 | 6/2010 | Warren et al. |
| 2010/0204671 | A1 | 8/2010 | Kraushaar et al. |
| 2010/0243099 | A1 | 9/2010 | Yodfat |

FOREIGN PATENT DOCUMENTS

| | | |
|---|---|---|
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 49-12690 | 5/1972 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 482670 | 4/2002 |
| WO | WO 84/04672 | 12/1984 |
| WO | WO 84/04673 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/05292 | 2/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | WO 02/064077 | 8/2002 |
| WO | WO 02/076540 | 10/2002 |
| WO | WO 2005/074860 | 8/2005 |
| WO | WO 2006/082350 | 8/2006 |

(56) References Cited

FOREIGN PATENT DOCUMENTS

| | | |
|---|---|---|
| WO | WO 2006/083333 | 8/2006 |
| WO | WO 2008/115102 | 9/2008 |
| WO | WO 2006/138184 | 12/2009 |

OTHER PUBLICATIONS

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009 (2 pages).

Extended European Search Report in EP07808894, dated Nov. 25, 2013, 4 pages.

* cited by examiner

BAG CONNECTOR

CROSS-REFERENCE TO RELATED APPLICATIONS

This application is a National Stage application under 35 U.S.C. §371 and claims the benefit under 35 U.S.C. §119(a) of International Application No. PCT/SE2007/050657, having an International Filing Date of Sep. 17, 2007, which is incorporated herein in its entirety.

TECHNICAL FIELD

The present invention relates to an attachable membrane for injection of fluid into a pierceable fluid container, or the withdrawal of fluid therefrom.

BACKGROUND OF THE INVENTION

Within several applications it is required to transfer pharmaceuticals or medicaments into a fluid container such as an infusion bag. Usually such infusion bags are filled with a transport liquid such as saline solution or glucose solution in order to simplify the drug preparation of such an infusion bag. Infusion bags are generally equipped with an injection port to provide medicaments and a piercing port to extract the fluid from the infusion bag to an infusion system and thereafter usually to a patient. These pre-manufactured ports on the infusion bags make them less flexible for use together with other injection devices. Manufacturing fluid containers having predetermined injection and extraction ports is also complicated in the sense that it adds manufacturing steps to the manufacturing of the fluid container itself.

One way of partly overcoming these drawbacks is described in the publication of WO 94/13247. The document describes a valve device comprising a valve body with a barrier membrane and a surrounding portion. The valve device has an adhesive surface located at the underside of the valve body to attach the valve body to the surface of an infusion bag. The valve device is manufactured in one piece of the same material and its main purpose is to be applied and handled on the occasion of use while retaining aseptic conditions even by persons of impaired sight. However even for persons with good sight the described solution may have drawbacks. Although allowing for any piercing member to be inserted through the membrane the document is completely silent about the drawback that the inserted piercing member may tear, rip, or even puncture the fluid container unless the user is cautious when handling the piercing member.

The publication of WO 82/03776 describes one way of trying to solve a related problem. The publication discloses a device for providing a barrier membrane to the surface of a flexible fluid container. The barrier membrane is adhered to the surface by an adhesive. Additionally the barrier membrane may be arranged with a flexible tube attached to a cylindrical casing. At the other end of the tube, the tube may be tightly connected to a holder for a hollow syringe needle. The syringe needle is surrounded by the tube which is slideable arranged to the syringe needle and is further provided with an arresting shoulder. The arresting shoulder of the syringe needle is in turn connected to connection means of a conventional type for a liquid conduit. The length of the tube is adapted such that its rear end rests against the holder of the syringe needle. When the needle is inserted the tube will also be inserted into the fluid container for as far as the arresting shoulder allows. The described solution provides for a rather complicated mechanism having moving parts for introducing or withdrawing a liquid into a flexible fluid container. There is a need for simpler solutions which maintain or even improve the safety of the process.

SUMMARY OF THE INVENTION

It is an object of the present invention to at least partly provide a solution to the above mentioned problems. It is further an object of the present invention to provide a simple attachable barrier membrane device which allows the user to safely introduce or withdraw liquid from a pierceable fluid container. The present objectives are achieved by an attachable membrane device for providing a pierceable liquid barrier membrane at the surface of a pierceable fluid container, such as an infusion bag, i.e. immediately adjacent to the surface of the pierceable fluid container or in the vicinity of said surface. The attachable membrane device have a fastening part comprising a fastening surface adapted to be attached to the surface of the pierceable fluid container and thereby provide a liquid tight seal between the fastening surface and the surface of the pierceable fluid container. The attachable membrane device is further provided with a barrier membrane part adapted to provide a liquid tight seal after penetration by a piercing member. The attachable membrane device is further arranged with connection means to connect and lock a piercing member device to the attachable membrane device from movement in a direction substantially longitudinal with the piercing member. The solution provides for a simple and direct connection to the barrier membrane onto which an injector or similar may be attached. The connection means also allows for a user to actually let go of a piercing member device after assembly with the attachable membrane device, allowing the user to perform other tasks e.g. nursing. Additionally, the connection means provides a grip for the user, which may be utilized when attaching the attachable membrane device to the fluid container.

The barrier membrane part and the fastening part may be separate parts arranged to be attached to each other. This embodiment is particularly advantageous when the fastening part needs specific properties or when the barrier membrane needs to have more pronounced sealing properties. The barrier membrane part and the fastening part may be integrally formed from one material. Such an embodiment may be advantageous from a manufacturing perspective since it allows for the manufacturing of the fastening part and the barrier membrane part in one step by e.g. moulding. The material used in this embodiment is chosen so as to provide for sufficient sealing properties while still impart sufficient strength to the fastening part. Preferably such embodiments are made from thermoplastic elastomers.

In one embodiment of the present invention the fastening surface is arranged with an adhesive to fasten the fastening part to the pierceable fluid container and thereby also provide for the liquid tight seal between the fastening surface and the pierceable fluid container. Although adhesive may be applied separate to the surface of the pierceable fluid container in order to attach the attachable membrane it is preferred that the fastening surface is provided with a binder such as an adhesive. Additionally such thin layer of adhesive may be provided with a protective layer preferably a silicone based release layer which is easy to peel off before attaching the barrier membrane device to the surface of the pierceable fluid container.

In a preferred embodiment of the present invention the connection means comprises a neck element having at least one guiding means, preferably two or more, to guide a piercing member device to a locked position. Preferably the neck element comprises two guiding means having the form of guiding grooves which during assembly with a piercing member device guide the piercing member device to a locked position. Usually such a piercing member device may be in the form of an injector. Once in the locked position the piercing member device is prevented from movement in a direction perpendicular to the fastening surface of the attachable membrane device.

In another embodiment of the present invention the fastening part of the attachable membrane device is arranged with a fluid channel extending from the fastening surface to the barrier membrane part. Such fluid channel has the main purpose of allowing a piercing member that is displaceable with respect to the locked piercing member device, such as a needle, to freely run through the fastening part without the need of penetrating any matter, except for the barrier membrane part, before piercing the fluid container. The embodiment simplifies the insertion of a piercing member while at the same time preventing the piercing member device from disengagement from the attachable membrane device.

In another embodiment of the present invention, the fastening part may comprise a compression volume. The compression volume may be arranged at the end of the fluid channel at the fastening surface of the fastening part. The compression volume is generally a substantially hollow space within the fastening part, or at least partly within the fastening part, which will allow the fastening part to be slightly more compressible. The fastening part may be provided with at least one compression volume, at least two compression volumes or at least three compression volumes. It may be arranged as above, in the proximity of the fastening surface but it may also be arranged at the proximity of the side edge of the fastening part or fully inside the fastening part. This enables a piercing function to the attachable membrane device without actually penetrating the fluid container by means of the piercing member device itself. Instead the actual piercing of the fluid container will take place after assembly with the piercing member device when the fastening part is compressed by a user. After compression the fastening part is preferably restored to its original shape and the piercing member is retracted back from the pierceable fluid container. Fluid may then be injected to the fluid container (or withdrawn). The compression volume will temporarily get filled with the fluid during this action. Leakage is effectively prevented by the liquid tight seal provided by the binding substance, e.g. an adhesive.

A piercing device may be attached to the connection means. Embodiments of the present invention having piercing devices are advantageous in combination with at least one compression volume. The piercing member of the piercing device is equipped with a piercing tip to pierce the pierceable fluid container. The piercing device may be either an integrated part of the connection means as illustrated in FIG. 3 or a separate part attached to the connection means (not shown). An arrangement like this allows for the attachable membrane device itself to actually pierce the fluid container rather than letting an attached piercing member do this. Preferably the piercing tip stretches from the compression volume into the fluid channel, this will prevent any material from being punched out, i.e. stamped out. Instead an opening will be formed having a tongue-shaped lid. This will secure the formation of a proper hole independently of the type of piercing member used.

In an additional embodiment of the present invention the connection means comprise a rigid material such as a rigid polymeric material. This allows for a sturdy connection with a piercing member device. In combination, or not, the fastening part may comprise a flexible material. By making the fastening part with a flexible material the risk of inducing damage to the fluid container is less as would otherwise be the case. Further will a force absorbing property be achieved. The fastening part may however comprise a rigid material such as a rigid polymeric material. This is especially advantageous when the connection means and the fastening part is constructed from the same material, i.e. when the fastening part and the connection means are integrally formed from one material. Preferably such an embodiment is formed by injection-moulding.

In one embodiment of the present invention a separate force absorbing material is arranged between the connection means and the fastening part. Such force absorbing material preferably comprises flexible material and is especially useful when the connection means and the fastening part are made of rigid material.

When a separate barrier membrane is used to create the barrier membrane properties, the separate barrier membrane is preferably attached in a slightly compressed state to the connection means. This can be done e.g. by means of the attachment method. The advantage of such an embodiment is that a piercing member of a relative large diameter can be used since the barrier membrane will flex back due to the compression. The barrier membrane is preferably compressed in the radial direction when welding the membrane to the connection means. The barrier membrane may as well be compressed in the direction in which the piercing member is intended to penetrate the barrier membrane, i.e. in a direction towards the centre of the pierceable fluid container.

DEFINITIONS

With the term "piercing member" is meant a needle or a needle like object or a hollow tube like object which is intended to pierce another object such as a membrane or similar for the purpose of transferring a fluid (liquid, gas or combinations thereof).

With the term "piercing member device" is meant any device onto which a piercing member may be arranged, e.g. an injector or a syringe or the like.

BRIEF DESCRIPTION OF THE DRAWINGS

The present invention will be described in greater detailed with referral to the following figures wherein.

DETAILED DESCRIPTION OF PREFERRED EMBODIMENTS

Figure 1:
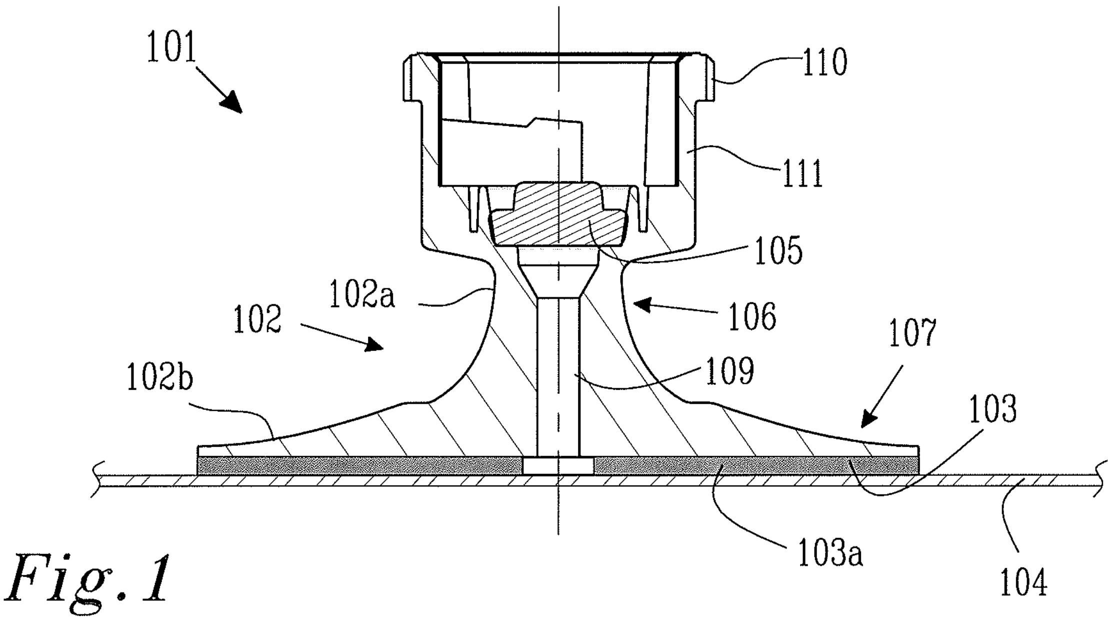
FIG. 1 shows a cross section of a first embodiment of the present invention wherein the connection means and the fastening part are made from the same material.

Referring to FIG. 1, FIG. 1 shows an attachable membrane device 101 according to the present invention for providing a pierceable liquid barrier membrane to the surface of a pierceable fluid container 104, such as an infusion bag. Said attachable membrane device has a fastening part 102 comprising a fastening surface 103 adapted to be attached to the surface of a pierceable fluid container 104 and thereby provide a liquid tight seal between the fastening surface 103 and the surface of said pierceable fluid container 104. The attachable membrane device 101 is further provided with a barrier membrane part 105 adapted to provide a liquid tight seal after penetration by a piercing member. The attachable membrane device 101 is further arranged with connection means 110 to connect and lock a piercing member device to the attachable membrane device 101.

The fastening surface 103 may be equipped with a thin layer of a binder such as an adhesive 103*a*. In the shown embodiment of the present invention the fastening part 102 can be said to comprise at least a first and a second fastening part section 102*a*, 102*b*. The first fastening part section 102*a* is specifically arranged to adapt the membrane device 101 to be used with piercing members having a determined work length. By the term determined work length it is meant that the length of the piercing member correlates to the length of the first fastening part section 102*a* so that only a pre-determined length of the piercing member can be inserted into the pierceable fluid container. The second fastening part section 102*b* is specifically arranged to create a relatively large fastening surface 103.

In the illustrated embodiment of the present invention the first fastening part section 102*a* has a diameter $d_a$ which is only approximately 20% of the diameter $d_b$ of the second connection section 102*b*. The first fastening section 102*a* has further a concave form to explicitly form a force absorbing part 106 on the fastening part 102. The force absorbing part 106 is formed in that part of the first fastening section 102*a* with the smallest diameter. The force absorbing part 106 allows for the fastening part 102 to absorb some of the forces that it is subjected to it by means of the connected fluid container or a user. Such forces may occur during or after connection. The purpose is to absorb forces acting on the attachable membrane device from the pierceable fluid container to reduce the risk of the attachable membrane device detaching from the surface 104 of the pierceable fluid container.

It has also been found that it is advantageous to have a flexible outer rim 107 on the second fastening part section 102*b*. By having a flexible outer rim the fastening part 102 is effectively prevented, to a certain extent, from causing harm to the pierceable fluid container when e.g. bending forces are applied to the attachable membrane device. Such a flexible outer rim 107 is preferably made from the same material as the fastening part 102 itself, however, in such case the thickness of the rim is small enough to provide for an acceptable flexibility. As indicated above the flexible outer rim 107 can be made from a different material than the fastening part 102.

Figure 2:
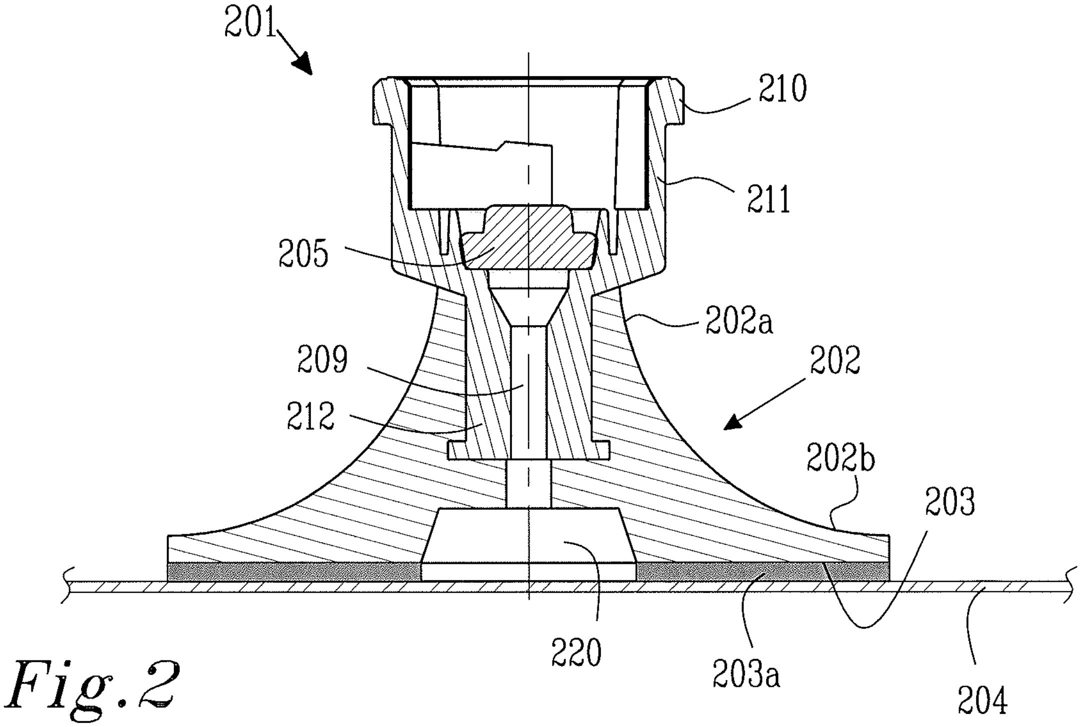
FIG. 2 shows a cross section of a second embodiment of the present invention wherein connection means and the fastening part are made from different material.

In FIG. 1 the fastening part 102 is equipped with a barrier membrane part 105 which provides for a liquid, and preferably gas tight seal around a piercing member during and after the pierceable fluid container has been pierced by a piercing member, such as a needle. The barrier member part 105 may be formed as an integral part of the fastening part 102 when the fastening part 102 is made of appropriate material. The barrier member part 105 can also be formed by a separate piece of material, e.g. when the fastening part 102 is made of a rigid material or when a specific material quality is required for the barrier member part 105. Alternatively, as illustrated in FIG. 2 the barrier membrane part may however not be arranged on the fastening part 102 but as shown on a part forming the connection means 210.

A fluid communication channel 109 arranged in the center of the fastening part 102 extends from the fastening surface 103 to the barrier membrane part 105. The fluid channel 109 is adapted to provide a channel for a piercing member which may be inserted through the channel to pierce the pierceable fluid container. Although a fluid channel is not a necessary feature of the present invention it is preferable since it will simplify the insertion of a piercing member since a piercing member only needs to penetrate the barrier member part 105 and not the whole of the fastening part in order to reach the surface 104 and thereafter the interior of the pierceable fluid container.

In some embodiments of the present invention the fluid channel does not need to extend the whole way from the barrier membrane to the fastening surface. It may well be that the fluid channel ends just above the fastening surface so that a second barrier membrane is created by means of the fastening part. Hence more generally, the attachable membrane device may be equipped with two barrier membranes in order to provide a secure liquid tight seal around the piercing member so as to prevent leakage of fluid. The fluid channel is in such an embodiment arranged between a first and a second barrier membrane.

As mentioned the attachable membrane device 101 comprises connection means 110 to connect and lock a piercing member device 550 to the attachable membrane device 101. Such piercing member device 550 may for instance be an injector assembly such as described in US 2003/0070726 A1 or e.g. as described in WO 2004/004806 (injection component 29). In any case the connection means 110 may comprise a cylindrical neck element 111 as described in greater detail in EP 1,434,549 A1 (in combination with a fluid container). The neck element 111 is in the current embodiment of the present invention equipped with two guiding members in which corresponding guiding means on the piercing member device may enter to connect and lock the piercing member device 550 to the connection means 110 and the attachable membrane device 101.

In the embodiment of the present invention shown in FIG. 1 the fastening part 102 and the connection means 110 are integrally formed from one material.

In FIG. 2 an attachable membrane device 201 for providing a pierceable liquid barrier membrane at the surface of a pierceable fluid container, such as an infusion bag, according to the present invention. Said attachable membrane device 201 has a fastening part 202 comprising a fastening surface 203 adapted to be attached to the surface of a pierceable fluid container 204 and thereby provide a liquid tight seal between the fastening surface 203 and the surface of said pierceable fluid container 204. The fastening surface 203 may be equipped with a thin layer of a binder such as an adhesive 203*a*. The attachable membrane device 201 is further provided with a barrier membrane part 205 adapted to provide a liquid tight seal after penetration by a piercing member. The attachable membrane device 201 is further arranged with connection means 210 to connect and lock a piercing member device to the attachable membrane device 201.

The attachable membrane device 201 is shown having a fastening part 202 with a first fastening part section 202*a* and a second fastening part section 202*b*. The connection means 210 similar to the one described with respect to FIG. 1, however, it is formed from a separate piece of material with respect to the fastening part 202. A cylindrical neck element 211 is equipped with two guiding members in which corresponding guiding means on a piercing member device may enter to connect and lock a piercing member device to the connection means 210 and the attachable membrane device 201. The connection means 210 further comprise an anchor element 212 onto which the fastening part 202 has been moulded, although other fastening methods may be used such as adhesive. In this embodiment the connection means 210 is formed to be rigid or formed from a rigid material in order to securely connect and lock a piercing member device.

The fastening part 202 may be formed from a flexible material such as a rubber-like material e.g. natural rubber, styrene rubber, urethane rubber or the like. Other suitable material may be thermoplastic elastomer (TPE) based on e.g. styrene, olefin, urethane, esters or amides. Any functional mixture of the above may also be suitable.

The connection means 210 is suitably formed to be rigid; preferably the connection means 210 is formed from a thermoplastic material such as polyethylene, polypropylene, polystyrene, polyurethane, polyvinyl chloride or the like. The connection means 210 may also be formed of a thermosetting plastic material such as epoxide esters (EP) or any other suitable thermosetting plastic material.

Further illustrated in FIG. 2 is a membrane barrier 205 (having exactly the same purpose as the barrier membrane describe earlier in the text relating to FIG. 1) which is attached to the connection means 210. A fluid communication channel 209 is arranged preferably in the center of the connection means 210 through which a piercing member of a piercing member device may be inserted. The fluid communication channel 209 extends from the barrier membrane 205 to the fastening surface 203.

In another embodiment of the present invention at least one compression volume 220 is arranged at the end of said fluid channel at the fastening surface 203 of said fastening part 202. The main purpose of such compression volume 220 is to allow for the fastening part 202 to flex in the longitudinal direction of an attached piercing member. It is also possible that the compression volume is located elsewhere as long as it provides for the intended function of allowing the fastening part 202 to be compressed. The feature allows for a piercing member to pierce a pierceable fluid container by simply compressing the attachable membrane device after a piercing member device has been connected and locked onto the attachable membrane device. When using this embodiment of the present invention it is not necessary that such piercing member is maintained inside the pierceable fluid container, it is enough that the piercing member makes a hole in the surface 204. Any fluid which is inserted into the pierceable fluid container may be temporarily maintained inside the compression volume 220 due to the liquid tight seal effectively provided for between the fastening surface 203 and the surface 204 of the pierceable fluid container before it is forced into the fluid container e.g. by pump means used by the user. The barrier membrane 205 prevents any such liquid from escaping out from the fluid communication channel 209.

Figure 3:
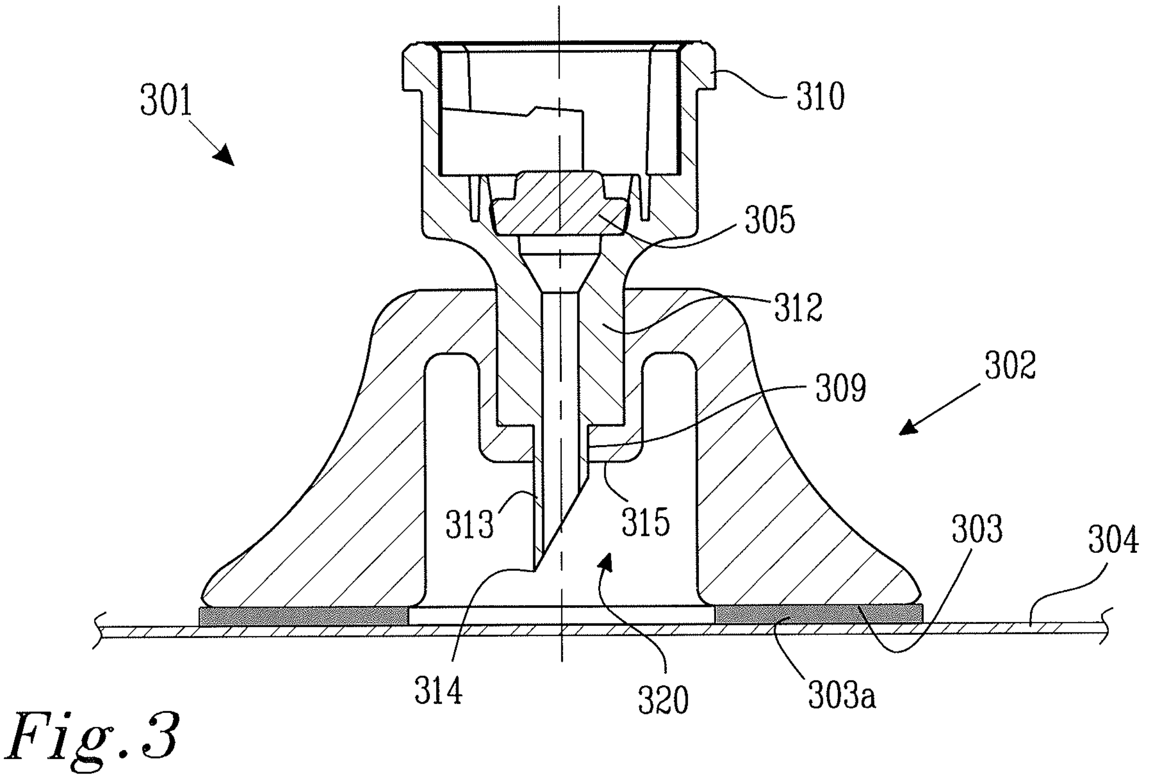
FIG. 3 shows a cross section of a third embodiment of the present invention having a piercing device.

FIG. 3 shows an attachable membrane device 301 according to the present invention for providing a pierceable liquid barrier membrane at the surface of a pierceable fluid container, such as an infusion bag. The attachable membrane device 301 has a fastening part 302 comprising a fastening surface 303 adapted to be attached to the surface of a pierceable fluid container 304 and thereby provide a liquid tight seal between the fastening surface 303 and the surface of the pierceable fluid container 304. The fastening surface 303 may be equipped with a thin layer of fastening means such as an adhesive 303*a*. The attachable membrane device 301 is further provided with a barrier membrane part 305 adapted to provide a liquid tight seal after penetration by a piercing member. The attachable membrane device 301 is further arranged with connection means 310 to connect and lock a piercing member device to the attachable membrane device 301.

In the shown embodiment in FIG. 3 the connection means 310 comprise an anchor element 312 onto which the fastening part 302 has been moulded. The anchor element 312 may further be equipped with a piercing device 313. It is well within the boundaries of the present invention that the anchor element 312 and the piercing device 313 are the same, i.e. the fastening part may be moulded (or fastened in any other way) directly onto the piercing device 313, in such case the piercing device 313 itself can be considered to be an anchor element. The piercing device 313 may be formed from a cylinder shaped, rigid material, preferably formed integrally from one piece of material with the connection means 310 when the connection means 310 is formed of a rigid material. The piercing device further comprises a piercing tip 314 which may be formed by cutting the piercing device 313 at an angle or more preferably by moulding the piercing device directly to have such a form. The piercing device 313 extends from the anchor part 312 into a compression volume 320 via a short fluid communication channel 309. The compression volume 320 is arranged at the fastening surface 303 of said fastening part 302. The main purpose of such compression volume 320 is to allow for the fastening part 302 to flex in the longitudinal direction of an attached piercing member (in principle perpendicular to the surface 304 of the pierceable fluid container). This allows for the piercing device to pierce a pierceable fluid container upon compression of the attachable membrane device. After piercing the surface of the pierceable fluid container 304 the piercing member does not need to be inserted into the fluid container in order to effectively transfer fluid via the attachable membrane device since fluid may be inserted without losses due to the liquid tight seals provided for by the sealing between the surface of the fluid container 304 and the fastening surface 303 as well as the sealing provided for by the barrier membrane 305.

The piercing tip 314 preferably extends into the fluid channel 309 as illustrated in FIG. 3. This configuration prevents a piece of material from being punched out from the surface 304 of the pierceable fluid container, instead a tongue-shaped, or horse-shoe shaped, lid is formed by the opening through which the fluid may be inserted, since the inner surface 315 of the compression volume 320 will effectively prevent the piercing device 313 from penetrating too far below the surface 304 of the fluid container. By having a lid formed next to the opening instead of punching a hole on the surface 304 of the pierceable fluid container, no loose material will contaminate the fluid inside the pierceable fluid container.

Figure 4:
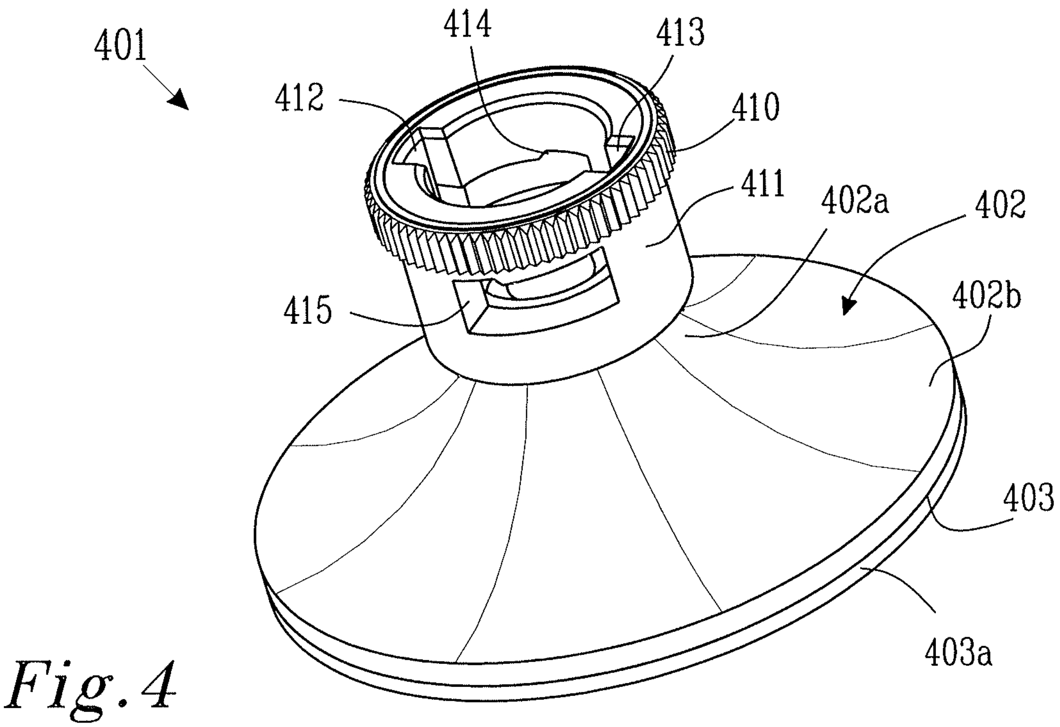
FIG. 4 shows the present invention in perspective.
Figure 5:
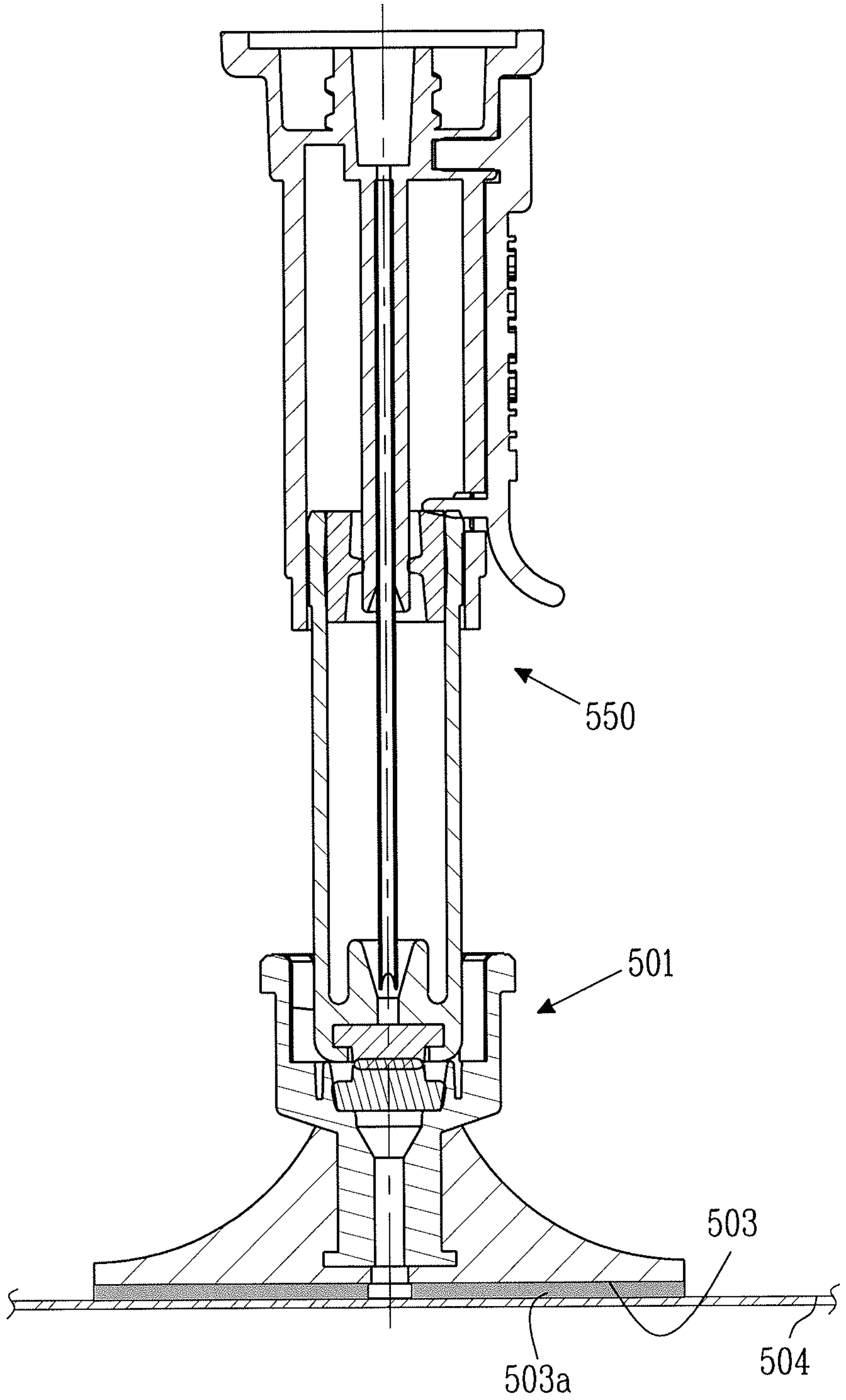
FIG. 5 shows a cross section of an embodiment of the present invention after assembly with a piercing member device.

FIG. 4 shows an embodiment of the present invention having connection means 410 to connect and lock a piercing member device (as seen in FIG. 5) to the attachable membrane device 401. The connection means 410 comprises a cylindrical neck element 411. The neck element 411 is in the current embodiment of the present invention equipped with two guiding members 412, 413 which will guide corresponding guiding means on the piercing member device to connect and lock the piercing member device to the connection means 410 and the attachable membrane device 401. The guiding members 412, 413 both lock the corresponding guiding means on the piercing member device at a lock position 414, 415.

Alternative, the connection means, to connect and lock a piercing member device from movement in a direction substantially longitudinal with the piercing member, may be in the form of a male connection part (not shown). However such male connection part must be equipped with a locking flange, preferably a circumferential locking flange, so that any connecting fluid container or coupling device can lock to said locking flange in order to prevent movement in a direction substantially longitudinal with the piercing member.

Further illustrated is a fastening part 402 having a first fastening part section 402*a* with a diameter $d_a$ which is only approximately 20% of the diameter $d_b$ of the second connection section 402*b*. The fastening part 402 has a concave form to form a force absorbing section on the fastening part 402. A thin layer of adhesive 403*a* is shown attached to a fastening surface 403.

FIG. 5 shows another attachable membrane device 501 having a fastener surface 503, according to the present invention in combination with a piercing member protection device 550 after assembly. The attachable member device 501 has been attached to the surface of a pierceable fluid container 504 with a thin layer of adhesive 503*a* which has been applied to the surface 504 just before attachment, as a preferred alternative, the adhesive layer may be applied in advance on the fastening surface 503 as described earlier. The fastening surface 503 has thereby been pressed against the adhesive to attach the attachable membrane device 501. The piercing member protection device 550 is shown in a secured position, i.e. the piercing member has not yet pierced the pierceable fluid container surface 504.

The invention claimed is:

1. An attachable membrane device for providing a pierceable liquid barrier membrane at the surface of a pierceable fluid container, wherein said attachable membrane device comprises a fastening part comprising a first fastening part section having a length that correlates to a pre-determined length of a piercing member and a second fastening part section comprising a fastening surface adapted to be attached to the surface of said pierceable fluid container, thereby providing a liquid tight seal between said fastening surface and the surface of said pierceable fluid container, a barrier membrane part adapted to provide a liquid tight seal after penetration by a piercing member wherein said fastening part is arranged with a fluid channel stretching from the fastening surface to said barrier membrane part, and a connector configured to substantially lock a piercing member device to said attachable membrane device from movement in a direction substantially longitudinal with said piercing member.

2. The attachable membrane device according to claim 1, wherein said barrier membrane part and said fastening part are separate parts arranged to be attached to each other.

3. The attachable membrane device according to claim 1, wherein said barrier membrane part and said fastening part are integrally formed from one material.

4. The attachable membrane device according to claim 1, wherein said fastening surface comprises an adhesive to fasten said fastening part to said pierceable fluid container, thereby providing for said liquid tight seal between said fastening surface and said pierceable fluid container.

5. The attachable membrane device according to claim 1, wherein said connector comprises a neck element having at least one guide to guide said piercing member device to a lock position.

6. The attachable membrane device according to claim 5, wherein said neck element comprises two guides having the form of guiding grooves.

7. The attachable membrane device according to claim 1, wherein said fastening part further comprises a compression volume arranged at the end of said fluid channel at the fastening surface of said fastening part.

8. The attachable membrane device according to claim 1, wherein said connector is arranged with a piercing device having a piercing tip to pierce said pierceable fluid container.

9. The attachable membrane device according to claim 7, wherein said connector is arranged with a piercing device having a piercing tip to pierce said pierceable fluid container, and wherein said piercing tip extends from said compression volume into said fluid channel.

10. The attachable membrane device according to claim 1, wherein said connector comprises a rigid material.

11. The attachable membrane device according to claim 1, wherein said fastening part comprises a flexible material.

12. The attachable membrane device according to any claim 11, wherein said flexible material is more flexible than the material from which said connector is formed.

13. The attachable membrane device according to claim 2, wherein said fastening part comprises a rigid material.

14. The attachable membrane device according to claim 13, wherein said fastening part and said connector are integrally formed from one material.

15. The attachable membrane device according to claim 14, wherein said fastening part and said connector are formed by injection-moulding.

16. The attachable membrane device according to claim 1, wherein said attachable membrane device comprises at least two barrier membranes of different material.

17. The attachable membrane device according to claim 1, wherein said connector is a male connection part comprising a locking flange.

18. The attachable membrane device according to claim 10, wherein said rigid material is a rigid polymeric material.

19. The attachable membrane device according to claim 13, wherein said rigid material is a rigid polymeric material.

* * * * *